(12) United States Patent
Isobe et al.

(10) Patent No.: US 7,268,215 B2
(45) Date of Patent: Sep. 11, 2007

(54) PHOTOPROTEIN DERIVED FROM OKINAWAN SQUID AND GENE ENCODING THE PHOTOPROTEIN

(75) Inventors: Minoru Isobe, Nagoya (JP); Tsukasa Matsuda, Nagoya (JP)

(73) Assignee: Nagoya University, Nagoya (JP)

( * ) Notice: Subject to any disclaimer, the term of this patent is extended or adjusted under 35 U.S.C. 154(b) by 47 days.

(21) Appl. No.: 10/835,180

(22) Filed: Apr. 30, 2004

(65) Prior Publication Data

US 2004/0191884 A1 Sep. 30, 2004

Related U.S. Application Data

(62) Division of application No. 09/863,339, filed on May 24, 2001, now Pat. No. 6,759,524.

(30) Foreign Application Priority Data

May 25, 2000 (JP) ............................ 2000-154786
May 1, 2001 (JP) ............................ 2001-133941

(51) Int. Cl.
*C07K 14/00* (2006.01)
*C07H 21/04* (2006.01)

(52) U.S. Cl. ................ 530/350; 435/252.3; 435/252.8; 435/243; 435/320.1; 435/69.1; 435/191; 544/346; 536/23.1

(58) Field of Classification Search ................ 530/350; 435/252.3, 252.8, 243, 320.1, 69.1, 191; 544/346; 536/23.1
See application file for complete search history.

(56) References Cited

OTHER PUBLICATIONS

Guo et al. , PNAS 101,9205-9210 (2004).*

M. Kuse et al., "Synthesis of 13C-Dehydrocoelenterazine and NMR studies on the bioluminescence of a *symplectoteuthis* model", Tetrahedron, Elsevier Science Publishers, Amsterdam, NL, vol. 56, No. 17, Apr. 2000, pp. 2629-2639.

M. Isobe et al., "Synthesis of 13C-Dehydrocoelenterazine and model studies on *symplectoteuthis* squid bioluminescence", Bioorganic and Medicinal Chemistry Letters, vol. 8, 1998, pp. 2919-2924.

H. Takahashi et al., "Photoprotein of luminous squid, *symplectoteuthis oualaniensis* and reconstruction of the luminous system", Chemistry Letters, 1994, pp. 843-846.

F.I. Tsuji et al., "K+ / Na+ -triggered bioluminescence in the oceanic squid *symplectoteuthis oualaniensis*", Proc. Nat. Acad. Sci. USA, vol. 78, No. 11, 1981, pp. 6719-6723.

M. Isobe et al., "Molecular mechanisms of bioluminescence of symplectin, a photoprotein from Okinawan squid, *symplectoteuthis oualaniensis L.*" Tennen Yuki Kagobutsu Toronkai Koen Yoshishu, vol. 42$^{nd}$., 2000, pp. 97-102.

M. Isobe et al., "Chemistry of photoproteins as interface between bioactive molecules and protein function" Pure & Appl. Chemistry, vol. 70, No. 11, 1998, pp. 2085-2092.

Shevchenko, Andrej, et al., "Rapid '*de Novo*' Peptide Sequencing by a Combination of Nanoelectrospray, Isotopic Labeling and a Quadrupole/Time-of-flight Mass Spectrometer" *Rapid Communications in Mass Spectrometry*.1997. pp. 1015-1024. vol. 2. John Wiley & Sons, Ltd.

* cited by examiner

*Primary Examiner*—Chih-Min Kam
(74) *Attorney, Agent, or Firm*—Buchanan Ingersoll & Rooney PC (57) ABSTRACT

By using a bioluminescence, a method for detection of a monovalent cation is provided and the method is a high sensitive and simple method. According to the present invention, an amino acid sequence of symplectin and a base sequence encoding the protein are provided. Symplectin is a photoprotein derived from *Symplectoteuthis oualaniensis* (okinawan squid). By using the photoprotein of the present invention, a monovalent cation can be detected by luminescence in the presence of a chromophore.

4 Claims, 4 Drawing Sheets

60(3)S:5'-CGG GAT CCT TYG ARC AYC ARG TNA THC C-3'
40AS:5'-GCC TCG AGT CRT TRT TRA ANG CNA CRT T-3'
BLP SP1:5'-ATG GAC CTG ATG GCA GAG AA-3'
MC-AS1:5'-TGR TAD ATN GGN GGN ARG TTN ACC CA-3'
FR29 AS:5'-GTY TGN ACR TCR TCR TCY TC-3'
photo-SP:5'-GAGACCAGTACCTATGGTAGCGG-3'
adapter primer:3'-RACE cDNA Synthesis Primer
         (SMART™ cDNA Amplification kit CLONTECH)

FIG. 4

● N-glycosylation site
| Cysteine residue

FIG. 5

Primers:
      EcoR1
PhPETS1:5'-TTGAATTCCCAAAAACAGATATGGAGAC-3'
PhPETS2:5'-TTGAATTCCTATTTTGGGAAGAAGGTTG-3'
PhPETA1:5'-AAGTCGACTTAGGAGGCGGCGTAAACATAAG-3'
          Sal1 stop Template:photogenic organ poly(A) + RNA

1st antibody : purified anti-symplectin antibody
2nd antibody : HPP-conjugated anti-mouse IgG

PHOTOPROTEIN DERIVED FROM OKINAWAN SQUID AND GENE ENCODING THE PHOTOPROTEIN

This application is a division of application Ser. No. 09/863,339 filed May 24, 2001, now U.S. Pat. No. 6,759,524, which claims foreign priority under 35 U.S.C. § 119 of Japanese Applications Nos. 2000-154,786 and 2001-133,941 filed in Japan on May 25, 2000 May 1, 2001, respectively.

BACKGROUND OF THE INVENTION

1. Field of the Invention

This invention relates to symplectin, which is a photoprotein derived from okinawan squid (*Symplectoteuthis oualaniensis*: Tobi-Ika). Moreover, this invention relates to an amino acid sequence of symplectin and a base sequence of gene encoding the protein. Furthermore, the present invention relates to a method for detection of a monovalent cation by monitoring luminescence, generated using said photoprotein in the presence of a chromophore.

2. Prior Art

Bioluminescence has been applied for various purpose, such as monitoring of concentration of a metal ion in a living cell, because some complementary factor is requisite for generation of luminescence. A chromophore is oxidized and then a high energy state intermediate (luminescent intermediate) is formed. It collapses to form a basal state and emission of luminescence occurs accompanied with such alteration of energy state. In a photogenic organism, emission of luminescent occurs efficiently using an enzyme.

The most classical bioluminescence is observed in firefly, which is well-known as luciferin-luciferase reaction. In luciferin-luciferase reaction, luciferin is converted to oxyluciferin via enzymatic reaction of luciferase in the presence of ATP and magnesium ion. It is the essential phenomenon involved in the photo-reaction. As the reaction mediated by firefly luciferase enables detection of luminescence with extremely high sensitivity, it is an important tool for investigation in the field of biochemistry. The gene encoding firefly luciferase has been already cloned. Then, heat-stable type luciferase is produced by genetic engineering technique using *E. coli* and it is commercially available.

For another example, aequorin, a blue fluorescent protein of jellyfish (*Aequorea victoria*) capable of emitting blue color luminescence, has been also known. Aequorin has a relatively low molecular mass of 21 kDa. Aequorin uptakes a chromophore such as coelenterazine and oxygen, then it is converted to an exited state (high energy state) using calcium ion as a trigger, thereby emits blue color luminescence. The color of jellyfish luminescence is actually blue color and not green color. However, green fluorescent protein (GFP) is assumed to receive energy from aequorin, thereby emitting green color luminescence.

The above luminescent system of jellyfish has been applied in the field of cell physiology and biochemistry. Emission of luminescence caused by aequorin is triggered by calcium ion. Then aequorin has been utilized to detect alteration of calcium ion concentration, such as for analysis on alteration of cytoplasmic calcium ion concentration caused by agonistic stimulation of intact cells, for example, by various hormones, agonists such as neurotransmitters or growth factors. Therefore, aequorin has attracted attention as a calcium sensor or a gene reporter, in the field of clinical biochemistry and cell physiology.

The above-mentioned method, utilizing luciferin or aequorin, is an excellent method for its high sensitivity. However, the ions which serves as the trigger of luminescence are magnesium ion and calcium ion for luciferin and aequorin, respectively. These are both divalent cations. Thus, there has been no means which enables detection of a monovalent cation using a photoprotein. The method utilizing a photoprotein is advantageous, because its sensitivity is extremely high and it is free from danger like experiments using a radioisotope. Therefore, a photoprotein which can detect a monovalent cation has been desired.

SUMMARY OF THE INVENTION

Thus, the inventors have noticed bioluminescent system of okinawan squid (*Symplectoteuthis oualaniensis*: Tobi-ika) from Okinawa, Japan. The luminescence of the squid was triggered by monovalent cations such as potassium, sodium or etc. and the inventors investigated on the luminescent system. In the luminescent system of okinawan squid, a monovalent cation acts as a trigger. Thus, the luminescent protein derived from okinawan squid is considered to be an excellent tool for detection of a monovalent cation.

One aspect of this invention of a protein derived from *Symplectoteuthis oualaniensis* (okinawan squid) having the following characteristics:

(1) emitting luminescence at wavelength of 470 nm by binding to dehydrocoeleneterazine or a dehydrocoeleneterazine derivative in the presence of potassium ion or sodium ion:

(2) having a molecular mass of approximately 60 kDa analyzed by SDS-polyacrylamide gel electrophoresis:

(3) dissolving into a solvent containing KCl at a concentration of 0.6M or higher while maintaining ability to emit luminescence: and

(4) decomposing by trypsin digestion to produce fragments having molecular masses of 40 kDa and 15 kDa.

According to the present invention, said dehydrocoeleneterazin derivative can be a compound selected from the group consisting of compounds represented by the following formula (1), (2) or (3):

(1)

wherein X is a halogen atom or methoxy group, a compound represented by the following formula:

(2)

wherein X represents a halogen atom, methoxy group or hydroxyl group, and Y and Z each represents hydrogen atom, a halogen atom, methoxy group or hydroxyl group, with the proviso that a case where both of Y and Z are hydrogen atoms is excluded, and a compound represented by the following formula:

(3)

wherein X and A each represents a halogen atom, methoxy group or hydroxyl group, and Y, Z, B and C each represents hydrogen atom, a halogen atom, methoxy group or hydroxyl group, with the proviso that cases where Y and Z are substituents selected from an atom or groups described above with both of B and C being hydrogen atoms and the case where all of Y, Z, B and C are hydrogen atoms are excluded.

Further aspect of this invention is a protein derived from *Symplectoteuthis oualaniensis* (okinawan squid) consisting of an amino acid sequence of following (a) or (b):

(a) an amino acid sequence represented by amino acid numbers 1 to 501 shown in SEQ:ID NO:1 in a sequence list, or (b) an amino acid sequence in which a part of said amino acid sequence (a) is deleted or another amino acid sequence is added to said amino acid sequence (a) or a part of amino acid sequence (a) is substituted with another amino acid sequence, the amino acid sequence (b) having characteristics that binds with dehydrocoeleneterazine by covalent bonding in the presence of potassium ion or sodium ion thereby emitting luminescence. The functional 40 kDa fragment of this protein, represented by amino acid numbers 1 to 370 shown in SEQ:ID NO:2 in a sequence list, is also within the range of this invention.

Moreover, further aspect of this invention is a method for detection of a monovalent cation, the method comprising formation of a conjugate adduct comprising the protein described above and an chromophore, thereby emitting luminescence from said conjugate adduct in the presence of a monovalent cation.

According to the present invention, said chromophore can be a compound selected from the group consisting of compounds represented by the following formula (4), (5), (6) or (7):

(4)

a compound represented by the following formula:

(5)

wherein X is a halogen atom or methoxy group,
a compound represented by the following formula:

(6)

wherein X represents a halogen atom, methoxy group or hydroxyl group, and Y and Z each represents hydrogen atom, a halogen atom, methoxy group or hydroxyl group, with the proviso that a case where both of Y and Z are hydrogen atoms is excluded, and a compound represented by the following formula:

(7)

wherein X and A each represents a halogen atom, methoxy group or hydroxyl group, and Y, Z, B and C each represents hydrogen atom, a halogen atom, methoxy group or hydroxyl group, with the proviso that cases where Y and Z are substituents selected from an atom or groups described above with both of B and C being hydrogen atoms and the case where all of Y, Z, B and C are hydrogen atoms are excluded.

Moreover, further aspect of this invention is a gene derived from *Symplectoteuthis oualaniensis* (okinawan squid) consisting of a base sequence of following (e), (f) or (g):

(e) a base sequence represented by base numbers 1 to 1646 shown in SEQ:ID NO:3 in a sequence list, (f) a base sequence in which a part of said base sequence (e) is deleted or another base sequence is added to said base sequence (e) or a part of base sequence (e) is substituted with another base sequence, the base sequence (f) encoding a protein having characteristics that binds with dehydro-coeleneterazine by covalent bonding in the presence of potassium ion or sodium ion thereby emitting luminescence, or (g) a base sequence that hybridizes with the base sequence (e) under stringent conditions.

Moreover, further aspect of this invention is a method for detection of a monovalent cation, the method comprising introduction of the gene described above into a cell, expression of protein encoded by said gene in the cell, formation of a conjugate adduct of the protein and a chromophore, thereby emitting luminescence from said conjugate adduct in the presence of a monovalent cation.

According to the present invention, said chromophore can be a compound selected from the group consisting of compounds represented by the following formula (8), (9), (10) or (11):

(8)

a compound represented by the following formula:

(9)

wherein X is a halogen atom or methoxy group, a compound represented by the following formula:

(10)

wherein X represents a halogen atom, methoxy group or hydroxyl group, and
Y and Z each represents hydrogen atom, a halogen atom, methoxy group or hydroxyl group, with the proviso that a case where both of Y and Z are hydrogen atoms is excluded, and a compound represented by the following formula:

(11)

wherein X and A each represents a halogen atom, methoxy group or hydroxyl group, and Y, Z, B and C each represents hydrogen atom, a halogen atom, methoxy group or hydroxyl group, with the proviso that cases where Y and Z are substituents selected from an atom or groups described above with both of B and C being hydrogen atoms and the case where all of Y, Z, B and C are hydrogen atoms are excluded.

Moreover, further aspect of this invention is a transformed *Escherichia coli* wherein the gene described above is introduced.

Moreover, further aspect of this invention is a method to produce a recombinant protein, the method comprising introduction of the gene described above succeeded by expression of protein encoded by said gene in *Escherichia coli*, said recombinant protein binds with dehydrocoeleneterazine by covalent bonding in the presence of potassium ion or sodium ion to form a conjugate adduct, thereby emitting luminescence from said conjugate adduct.

DETAILED DESCRIPTION OF THE INVENTION

Figure 1:
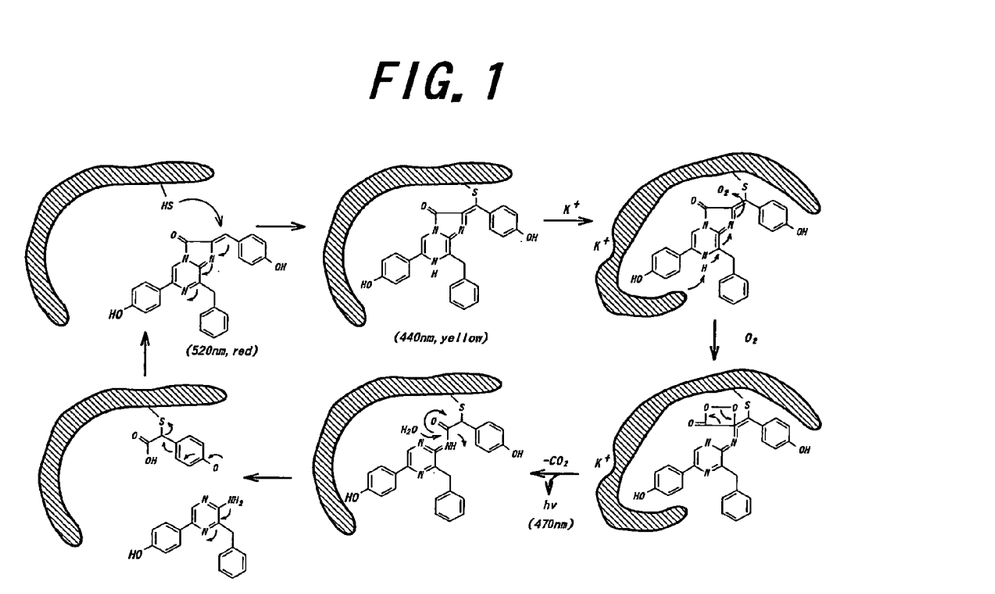
FIG. 1 is a schematic view showing the assumed mechanism of emission of luminescence observed in okinawan squid.

Okinawan squid has a large photogenic organ on its body. Here, a photoprotein symplectin is involved in the luminescence emitting system. Dehydrocoeleneterazine is bounded to symplectin protein by covalent bonding and an oxygen molecule and a monovalent cation (such as potassium, sodium, etc.) are required for emission of luminescence. That is, dehydrocoeleneterazine (chromophore) is incorporated into the protein to form a conjugate adduct by covalent bonding. Then the chromophore is converted to its reduced form in the presence of a monovalent cation, which result in emission of luminescence. It is assumed that, conformation of the photo-protein is altered in the presence of a monovalent cation, whereby a chemical reaction accompanied with emission of luminescence occurs. This is the reason why a monovalent cation serves as a trigger of luminescence in the photo-system of okinawan squid. The assumed luminescent mechanism of okinawan squid, clarified using a model system of glutathione, is shown in FIG. 1.

In the luminescent system of okinawan squid, dehydrocoeleneterazine can be used as a chromophore and dehydrocoeleneterazine binds to symplectin, the photoprotein of this invention.

Incidentally, the inventors have utilized a system using crude apo-protein without a chromophore and added the above-mentioned chromophore or its derivative to the system, thereby reconstituted the photoprotein. As the result of such experiment, emission of luminescence was confirmed.

The photoprotein of okinawan squid has a low solubility and there is no conventional method for research of the protein. When a surfactant to solubilize the membrane protein is used, luminescent activity of the okinawan squid photoprotein would be disrupted. By addition of KCl (a caotropic salt) to a buffer, the protein can be solubilized without disrupting its activity. The effects of various kinds of salts on the objective protein are examined in the terms of extraction efficiency and luminescent activity. As the result, it was found that KCl was the most suitable. Also, different from the case of aequorin, luminescence of symplectin was not triggered by a divalent cation. Enzymatic characteristic of okinawan squid was investigated. As a result, it was found that the optimum pH was 8 and the optimum temperature was about 20° C. (Isobe M. et al., Pure and Appl. Chem., (1998) Vol.70, 2085-2092).

As described in the following Examples, the present inventors have extracted the photoprotein derived from okinawan squid in a buffer containing KCl. Moreover, the inventors have determined the base sequence by PCR cloning and determined the amino acid sequence. The structure of symplectin of the present invention, which is a photoprotein derived from okinawan squid, can be specified by the amino acid sequence described in Sequence ID. NO:1 of the sequence List. The above-mentioned chromophore is covalently bonded to the protein shown in the amino acid sequence, then emission of luminescence occurs in the presence of a monovalent cation as a trigger. The protein specified by said amino acid sequence shows a molecular mass of about 60 kDa determined by SDS-polyacrylamide gel electrophoresis (SDS-PAGE).

The polypeptide consisting of an amino acid sequence in which a part of said polypeptide specified by amino acid sequence shown in SEQ ID NO: 1 is deleted, substituted or added with another amino acid sequence means a polypeptide in which 20 or less, preferably ten or less, and more preferably five or less amino acids of the sequence is deleted, substituted or added to the amino acid sequence shown in SEQ ID NO: 1 in a sequence list. Moreover, such polypeptide exhibits homology 70% or more, preferably 80% or more and still preferably 90% or more with the amino acid sequence shown in SEQ ID NO: 1 in a sequence list. Such polypeptide is also within the range of this invention so far as it exhibits the characteristic as the photoprotein symplectin, that binds with a chromophore by covalently bonding in the presence of a monovalent cation thereby emitting luminescence.

Also, as shown in the following Examples, treatment of said protein with trypsin results in decomposition into two fragments of 40 kDa and 15 kDa. Here, the 40 kDa fragment, corresponding to C-terminal portion of the original protein, is involved in the photogenic function of the protein. Amino acid sequences of the above-mentioned 40 kDa obtained by the trypsin digestion is shown in SEQ ID NO: 2 in a sequence list. The polypeptide having the amino acid sequence shown in Sequence ID. NO: 2 in a sequence List is also within the scope of the present invention.

The polypeptide consisting of an amino acid sequence in which a part of said polypeptide specified by the amino acid sequence shown in SEQ ID NO: 2 is deleted, substituted or added with another amino acid sequence means a polypeptide in which 20 or less, preferably ten or less, and more preferably five or less amino acids of the sequence is deleted, substituted or added to the amino acid sequence shown in SEQ ID NO: 2 in a sequence list. Such polypeptide is also within the range of this invention so far as it exhibits characteristic as the photoprotein symplectin, that binds with a chromophore by covalent bonding in the presence of a monovalent cation thereby emitting luminescence.

Moreover, cDNA of the gene encoding symplectin protein is specified by the base sequence shown in SEQ ID NO: 3 is a sequence list. The base sequence described in SEQ ID. NO:3 in a sequence list is a base sequence corresponding to its full length cDNA. The sequence includes open reading frame that encodes 489 amino acids residues, which corresponds to the region from the thirteenth residue phenylalanine to serine residue of the C-terminal shown in SEQ ID. NO: 1 in a sequence list.

With regard to many amino acids, one amino acid is encoded by plural base sequences of DNA. Therefore, plural genes, other than native gene of this invention, might encode amino acid sequence of symplectin identified by the present invention. The gene of this invention is not to be limited to only native gene and intended to include many other sequences encoding the photoprotein identified by the present invention.

According to technique of gene recombination, artificial modification can be achieved at a specific site of basic DNA, without alteration or with improvement of basic characteristic of said DNA. Concerning a gene having native sequence provided according to this invention or modified sequence different from said native sequence, it is also possible to perform artificial modification such as insertion, deletion or substitution to obtain gene of equivalent or improved characteristic compared with said native gene. Moreover, a gene with such mutation is also included in the range of this invention. That is, the gene, consisting of a base sequence hybridizes with said base sequence shown in SEQ ID NO: 3 in a sequence list under stringent condition, means a gene in which 20 or less, preferably ten or less, and more preferably five or less bases of the sequence is deleted, substituted or added to the base sequence shown in SEQ ID NO: 3 in a sequence list. Moreover, such gene exhibits homology 70% or more, preferably 80% or more and still preferably 90% or more with the base sequence shown in SEQ ID NO: 3 in a sequence list. In addition, such gene hybridizes with the base sequence shown in the SEQ ID NO: 3 in a sequence list under stringent condition. Such gene is also within the range of this invention so far as it encodes a polypeptide having characteristic as the photoprotein symplectin, that binds with a chromophore by covalent bonding in the presence of a monovalent cation thereby emitting luminescence.

The photoprotein of the present invention is particularly useful for detection of a monovalent cation with high sensitivity. Bioluminescence can be detected with extremely high sensitivity of approximately $10^{-16}$ mol.

Therefore, it is possible to detect a monovalent cation rapidly easily and simply, with sensitivity equivalent to or higher than that of a radioisotope. Thus, the photoprotein of the present invention has excellent characteristics as a sensor available for detection of a monovalent cation, particularly potassium ion or sodium ion.

In concrete, the photoprotein of the present invention or the gene encoding the photoprotein can be utilized for a clinical reagent for analysis in the field of medical treatment or for a research reagent for biochemical research. In the field of clinical analysis, for the purpose of in vitro (in a test tube) detection of a monovalent cation, the photoprotein of the present invention is particularly useful. Not only for the above purpose, the photoprotein of the present invention can be utilized for detection of infinitesimal alteration of monovalent cation concentration in a cell. Aequorin, a photoprotein of the above-mentioned jellyfish, has been used as an indicator for detection of calcium ion concentration in a cell, as a conventional technique in this technical art. It is assumed that the photoprotein of the present invention can be utilized as an indicator for detection of a monovalent cation, in the manner similar to aequorin. In regard to aequorin, a technique applicable for detection of alteration of calcium ion concentration in an intact cell has been established, using a system in which a gene encoding aequorin is expressed in a cell. Concerning the gene and the polypeptide of the present invention, the base sequence and the amino acid sequence have been determined by the present invention. Therefore, they would be utilized in the same manner as aequorin. Particularly, for the investigation on the function of a nerve cell, it is very important to detect infinitesimal alteration of potassium ion concentration. For example, alteration of an infinitesimal amount of monovalent cation in a cell can be measured by introduction of the photoprotein of the present invention, using a technique such as microinjection or etc. Also, the same effects can be obtained by introduction of the gene encoding the photoprotein of the present invention, succeeded by expression of the gene. In these cases, a chromophore can be provided externally. In a plant, particularly, the chromophore can be absorbed from its root.

Incidentally, the present inventors have established a method for detection of phosphatase activity with high sensitivity, using luciferin-luciferase system of firefly. Luciferin phosphate is a compound wherein phosphate group is bonded to luciferin, which is a chromophore. When luciferin phosphate was treated by phosphatase, a chromophore luciferin was formed, enzymatic reaction by luciferase was performed using the formed luciferin as a substrate, then emission of luminescence can be detected. Meanwhile, luciferin phosphate does not serve as a substrate of luciferase and generation of luminescence does not occur. That is, in the absence of luciferin formed by the enzymatic reaction by phosphatase, luminescence can not be detected. Therefore, the luminescent intensity correlates with the phosphatase activity. That is, enzymatic activity of phosphatase can be displaced to intensity of bioluminescence.

The okinawan squid photoprotein of the present invention can be also utilized for measurement of enzymatic activity of an enzyme according to the same principle. Explaining measurement of phosphatase activity using an example, the method comprises formation of a chromophore derivative, in which phosphate group is bonded to the chromophore such as dehydrocoelenterazine to form a substrate of phosphatase, succeeded by performance of enzymatic reaction using the derivative as a phoaphatase substrate. The chromophore formed by the enzymatic reaction is covalently bonded to okinawan squid photoprotein and emits luminescence in the presence of a monovalent cation. Therefore, enzymatic reaction can be measured by detection of luminescence. Measurement according to the same principle can be applied to various kinds of enzymes other than phosphatase, so far as the chromophore can be converted to substrate of the objective enzyme.

In the following Examples, the present invention is explained in more detail, but the present invention is not to be limited by the above descriptions nor the following examples. It should be noted that any conventional modification known in this technical field is included in the range of this invention.

EXAMPLES

From photogenic organ of okinawan squid, collected at the sea area of Okinawa Prefecture Japan, the photoprotein having a molecular mass of 60 kDa was separated and purified as a luminescent ability as an index. This photoprotein was soluble in a solution containing KCl at a concentration of more than 0.6M. At first, homogenate of the photogenic organ containing symplectin was washed by KCl solution (pH 6.0) of 0.4M. Then, it was extracted with a KCl solution of 0.6M, and a portion thereof was added to a buffer having pH of 8.0 to confirm the luminescent ability. Because of high salt concentration, means of chromatography applicable for purification of the extract was limited.

Figure 2:
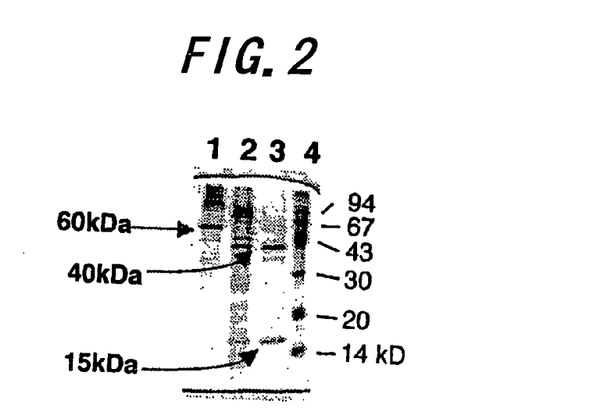
FIG. 2 is a photograph showing the result of SDS-PAGE analysis of the present photoprotein, with and without subjection to trypsin digestion.

When the purified protein was hydrolyzed by trypsin, two products having molecular masses of 40 kDa and 15 kDa were produced from the original protein of 60 kDa (FIG. 2). In FIG. 2, lane 1 shows the result original protein before trypsin digestion, lane 2 shows that of trypsin digested crude protein, lane 3 shows that of trypsin digested purified protein, and lane 4 shows that of molecular weight marker, respectively. Fragments of 40 kDa and 15 kDa were recognized after trypsin digestion, particularly in lane 3 corresponding to the purified protein. When the ability to emit luminescence was investigated, both of 60 kDa protein of and 40 kDa proteins exhibited luminescence. On the other hand, the 15 kDa protein did not give luminescence. However, the amino acid sequence of the 15 kDa protein was the same as the N-terminal amino acid sequence of the 60 kDa protein. Then it was revealed that the 15 kDa protein corresponded to the N-terminal sequence of symplectin. Incidentally, the active region responsible for the photogenic function would exist at the C-terminal portion corresponding to the 40 kDa protein.

The protein thus purified was hydrolyzed by enzyme to produce peptide fragments, then partial amino acid sequence of these fragments were determined by analysis using nano-LC-Q-TOF-MS/MS. Chromatography and mass-spectrum analysis (MS/MS spectrum) were carried out in such manner and partial amino acid sequences of several peptide fragments were determined. As the result, the N-terminal amino acid sequence was found to be YVRPVSSWK (ESQ ID NO:13). Based on the partial amino acid sequences of the peptide fragments thus determined, oligonucleotide primers were synthesized to utilize for amplification of cDNA by PCR.

Next, from the photogenic organ of okinawan squid, RNA was purified and cDNA pool was prepared by reaction utilizing reverse transcriptase. Using cDNA thus obtained as a template, polymerase chain reaction (PCR) was performed using the above-mentioned synthetic oligonucleotide primers and cDNA fragment of the photoprotein was amplified. Sequences of the primers used for following PCR cloning were shown below.

minal amino acids determined by the nano-LC-Q-TOF-MS/MS was added to the determined sequence. As the result, full length amino acid sequence of okinawan squid photoprotein was determined and it was composed of 501 amino acids. The amino acid sequence of symplectin thus obtained is shown in Sequence ID. NO:1 in a sequence list. The calculated molecular mass of the polypeptide was 57,463 and the molecular mass was slightly smaller than 60 kDa, which was evaluated by SDS-PAGE. Moreover, in the amino acid sequence comprising the above-mentioned 501 amino acids, the sequence corresponding to the 40 kDa fragment is shown in Sequence ID. NO:2 in a sequence List. As described above, the 40 kDa fragment obtained by trypsin digestion exhibited photogenic activity.

Figure 4:
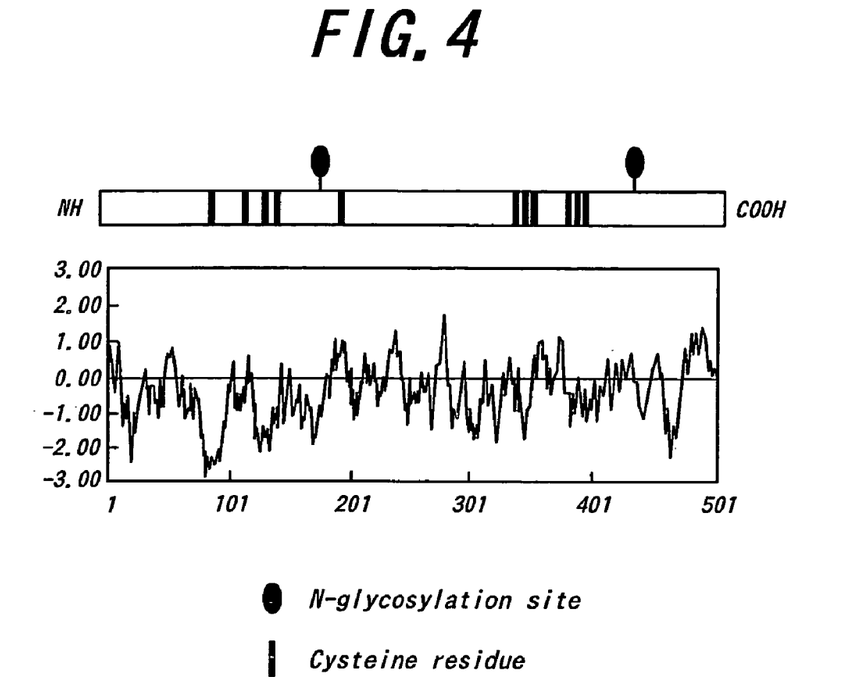
FIG. 4 is a figure showing schematic view of structure of the present photoprotein and hydropathy profile.

In the sequence of symplectin, a photoprotein of okinawan squid, there are two putative N-glycosylation sites. This notion indicates the possibility that, this photoprotein might be a glycoprotein. The results of amino acid content analysis and hydropathy profile showed that this protein does not exhibit high degree of hydrophobic property, though the solubility of this protein into an aqueous solution is low. A schematic drawing of structure of symplectin is shown in the upper portion of FIG. 4 and the result of hydrophacy profile is shown in the lower portion of FIG. 4. The amino acid sequence of okinawan squid protein did not exhibit homology with the known photoproteins at all. The results showed that this photoprotein derived from the squid was a novel photoprotein, as suggested from monovalent cation dependency for emission of luminescence.

```
60(3)S:     5'-CGG GAT CCT TYG ARC AYC ARG TNA THC C-3'    (SEQ ID NO: 4)

40AS:       5'-GCC TCG AGT CRT TRT TRA ANG CNA CRT T-3'    (SEQ ID NO: 5)

BLP-SP1:    5'-ATG GAC CTG ATG GCA GAG AA-3'               (SEQ ID NO: 6)

MC-AS1:     5'-TGR TAD ATN GGN GGN ARG TTN ACC CA-3'       (SEQ ID NO: 7)

FR29 AS:    5'-GTY TGN ACR TCR TCR TCY TC-3'               (SEQ ID NO: 8)

photo-SP:   5'-GAGACCAGTACCTATGGTAGCGG-3'                  (SEQ ID NO: 9)
```

Adapter primer: 3'-RACE cDNA synthetic primer (SMART™ cDNA amplification kit: available from Clontech)

Figure 3:
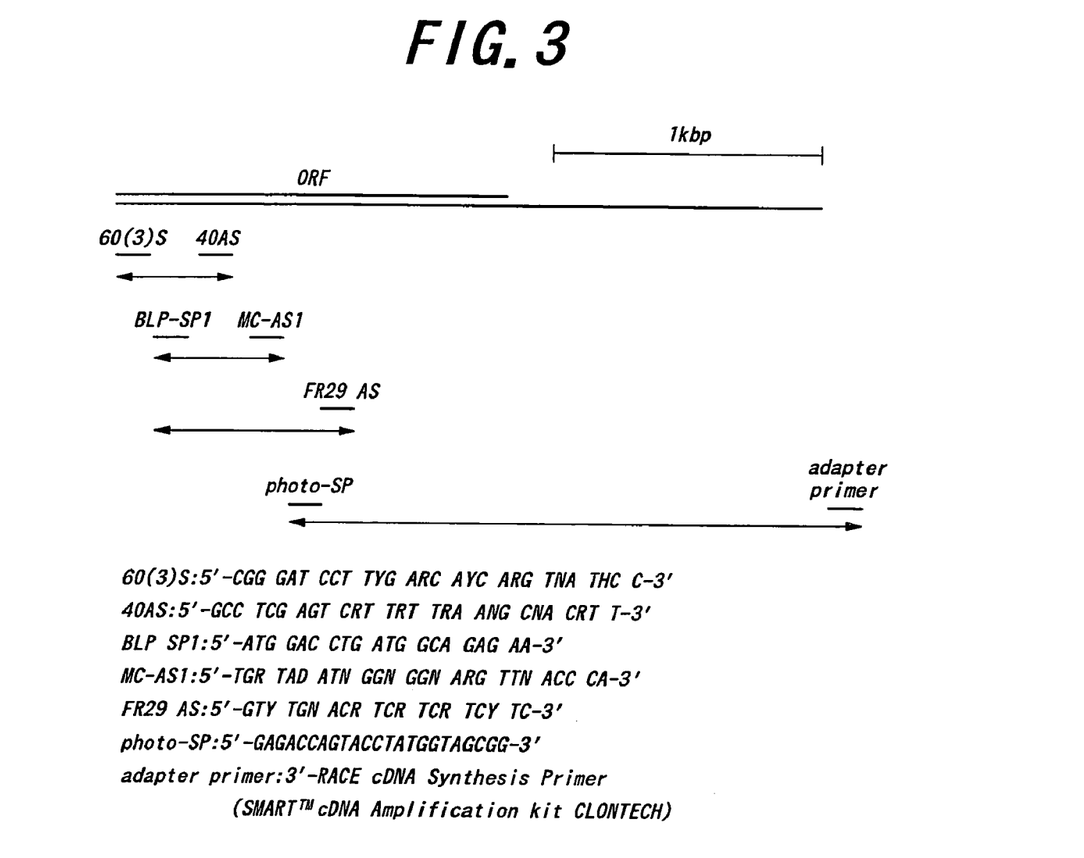
FIG. 3 is a figure showing strategy of PCR cloning, utilized to obtain cDNA of the present photoprotein.

First, amplification by PCR was performed using 60(3)S and 40AS, primers designed based on the partial amino acid sequence. Based on the sequence, BLP-SP1, a primer specific for the gene, was synthesized. Moreover, based on the above-mentioned partial amino acid sequence two kinds of primers (MC-AS1 and FR29 AS) were synthesized. They were further elongated to the 3' region. Finally, using the another primer specific for the gene, 3'-RACE (rapid amplification of cDNA ends) was performed using SMART™ cDNA amplification kit (available from Clontech) and the full length DNA was cloned. The strategy of the PCR cloning adopted for this experiment was shown in FIG. 3.

As a result, cDNA shown in Sequence ID. NO:3 in a sequence list was obtained and it was comprised of 1646 bases. This cDNA contained a base sequence encoding a polypeptide comprising 489 amino acid residues as the constructive gene, and the base sequence corresponds to the amino acid sequence from the 13$^{th}$ phenylalanine to serine at the C-terminal. The sequence comprising the twelve N-ter- From homology research of the 60 kDa photoprotein using BLAST program, it was revealed that two proteins exhibited homology with this photo-protein. One of which is biotinidase (EC 3.5.1.12), a soluble enzyme which hydrolyzes biocytin to form biotin and lysine. Another one is vanine, a GPI-anchord type protein. The membrane protein is expressed in perivascular thymic stromal cells, and suggested to be a homing receptor for hematopoietic precursor cells to migrate into thymus. Only limited homology was recognized between the squid photoprotein and these protein derived from mammals. However, eleven cystein residues were preserved in these three proteins.

Figure 5:
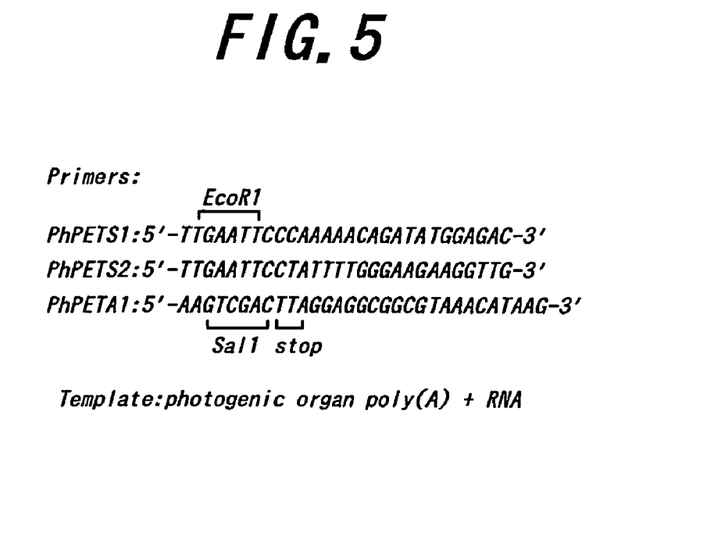
FIG. 5 is a figure showing primers and template utilized for PCR amplification.
Figure 6:
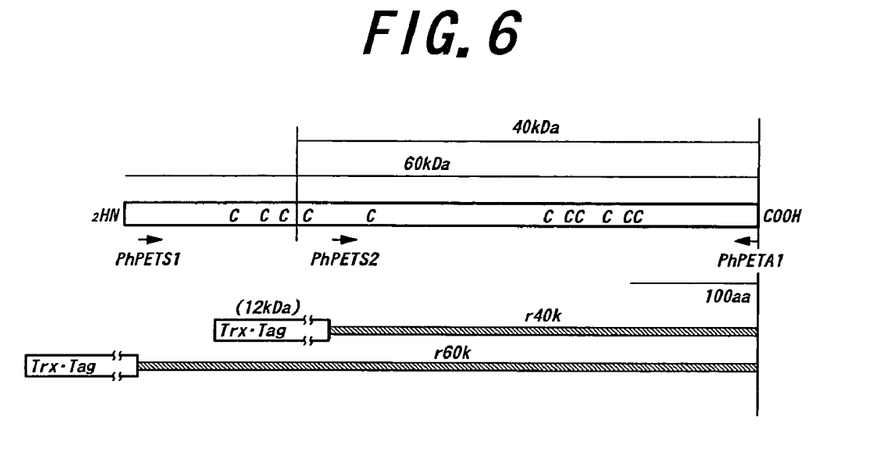
FIG. 6 is a figure showing strategy for PCR amplification of the cDNA of the present photoprotein.

The cDNAs encoding symplectin protein of this invention and 40 kDa fragment thereof were amplified by PCR using following sense primers (PhPETS1, PhPETS2) and a common antisense primer(PhPETA1). As well, poly(+)RNA of the photogenic organ was utilized as a template for PCR amplification. As shown in FIG. 5, restriction sites (EcoRI site and SalI site) were inserted into these primers. Moreover, as shown in FIG. 6, cDNAs encoding full length symplectin protein of 60 kDa or its 40 kDa fragment were amplified.

```
PhPETS1: 5'-TTTGAATTCCCAAAAACAGATATGGAGAC-3'    (SEQ ID NO: 10)

PhPETS2: 5'-TTGAATTCCTATTTTGGGAAGAAGGTTG-3'     (SEQ ID NO: 11)

PhPETA1: 5'-AAGTCGACTTAGGAGGCGGCGTAAACATAAG-3'  (SEQ ID NO: 12)
```

The PCR products were separated on an agarose gel succeeded by digestion with EcoRI and SalI. Then it was ligated to EcoRI and SalI site of pET-32a(+) to construct a vector. The vector was designated pET-60 and it was utilized for expression of symplectin protein. The E. coli strain BL21(DE3)pLysS, transformed by pET-60, was grown in Luria broth (LB) at 37° C. Expression of the protein was induced by addition of isopropyl-1-thio-b-D-galactopyranoside (IPTG). The cells were harvested by centrifugation and lysed by sonication in a buffer. The homogenate was centrifuged, and the supernatant was subjected to affinity chromatography using His-Bind Resin. The fusion protein with thioredoxin was purified by a step-wise manner elution with varied imidazole concentrations. The recombinant symplectin protein was obtained as a fusion protein with thioredoxin, according to the manipulation described above.

Figure 7:
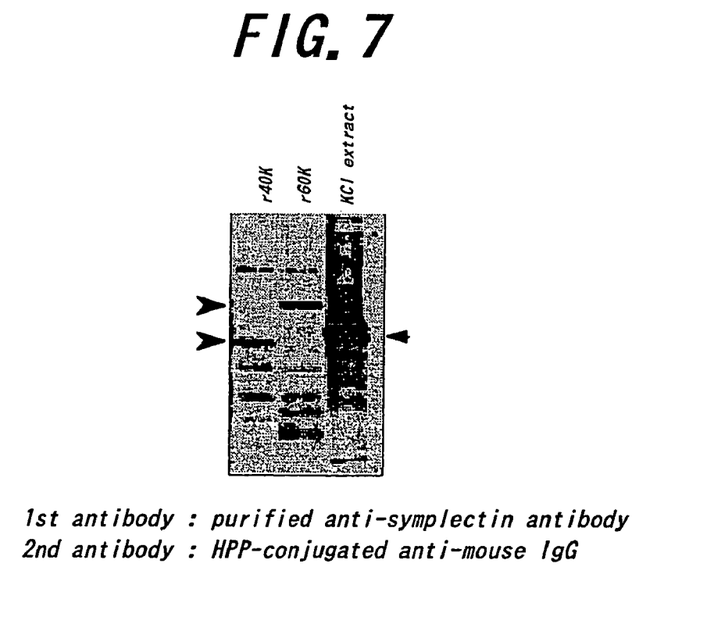
FIG. 7 is a photograph showing the result of Western blot analysis of the obtained recombinant protein.

As the result of SDS-PAGE of the cell lysate, symplectin and its 40 kDa fragment were detected. Furthermore, Western blot analysis was performed and these bands were stained by anti-symplectin antibody. It indicates that the protein according to this invention is expressed as a recombinant protein. The result of Western blot analysis is shown in FIG. 7. In FIG. 7, anti-symplectin antibody was used as the 1$^{st}$ antibody and HRP-conjugated anti-mouse IgG was used as the 2$^{nd}$ antibody. Moreover, lane 1 is recombinant protein of 40 kDa fragment, lane 2 is recombinant protein of full length 60 kDa protein and lane 3 is crude extract. As indicated by arrows in FIG. 7, proteins exhibiting reactivity with the antibody was detected at the positions corresponding to 75 kDa and 55 kDa.

The recombinant symplectin protein was subjected to bioluminescence assay. The recombinant symplectin protein was suspended in a buffer, mixed with chromophore dehydrocoeleneterazine, then protein-chromophore complex was formed by incubation at 37° C. for 30 min. The alkaline buffer (pH9.8) was added to increase pH of the protein-chromophore complex solution and the bioluminescence reaction was initiated. The generated luminescence was monitored by lumiphotometer and obvious luminescence was detected as the result. The ability of recombinant symplectin protein to emit luminescence indicates that cDNA of symplectin protein actually encodes photoprotein derived from okinawan squid. According to the present invention, an amino acid sequence of symplectin, a photoprotein derived from okinawan squid (Symplectoteuthis oualaniensis : Tobi-Ika) and a base sequence of the gene encoding said protein were provided. The photoprotein of the present invention enables detection of a monovalane cation by monitoring chemiluminescence in the presence of a chromophore.

The invention claimed is:

1. An isolated protein selected from the group consisting of:

(a) a protein comprising the amino acid sequence of amino acids 1 to 501 of SEQ ID NO:1 ;

(b) a protein comprising an amino acid sequence of amino acids 1 to 501 of SEQ ID NO:1 containing up to 20 amino acid substitutions, deletions or insertions, wherein the protein binds covalently with dehydrocoelenterazine in the presence of potassium ion or sodium ion, thereby emitting luminescence; and

(c) a protein consisting of the amino acid sequence of amino acids 1 to 501 of SEQ ID NO:1.

2. A method for detection of a monovalent cation, the method comprising forming a conjugate adduct comprising the protein according to claim 1 and a chromophore, thereby emitting luminescence from said conjugate adduct in the presence of a monovalent cation, wherein said chromophore is a compound selected from the group consisting of a compound represented by the following formula (8):

(8)

a compound by the following formula (9):

(9)

where X is a halogn atom or methoxy group, a compound represented by the following formula (10):

(10)

wherein X represents a halogen atom, methoxy group, or a hydroxyl group, and Y and Z each represents a hydrogen atom, a halogen atom, methoxy group, or hydroxyl group, with the proviso that a case where both Y and Z are hydrogen atom is excluded, and a compound represented by the following formula (11):

(11)

wherein X and A each represents a halogen atom, methoxy group, or hydroxyl group, and Y, Z, B, and C each represents a hydrogen atom, a halogen atom, methoxy group, or hydroxyl group, with the proviso that cases where Y and Z are substituents selected from an atom or groups described above with both B and C being hydrogen atoms and the cases where all of Y, Z, B, and C are hydrogen atoms are excluded.

3. An isolated protein selected from the group consisting of:
   (a) a protein comprising the amino acid sequence of amino acids 1 to 370 of SEQ ID NO:2;
   (b) a protein comprising an amino acid sequence of amino acids 1 to 370 of SEQ ID NO:2 containing up to 20 amino acid substitutions, deletions or insertions, wherein the protein binds covalently with dehydrocoelenterazine in the presence of potassium ion or sodium ion, thereby emitting luminescence; and
   (c) a protein consisting of the amino acid sequence of amino acids 1 to 370 of SEQ ID NO:2.

4. A method for detection of a monovalent cation, the method comprising forming a conjugate adduct comprising the protein according to claim 3 and a chromophore, thereby emitting luminescence from said conjugate adduct in the presence of a monovalent cation, wherein said chromophore is a compound selected from the group consisting of a compound represented by the following formula (8):

(8)

a compound represented by the following formula (9):

(9)

where X is a halogen atom or methoxy group, a compound represented by the following formula (10):

(10)

wherein X represents a halogen atom, methoxy group, or a hydroxyl group, and Y and Z each represents a hydrogen atom, a halogen atom, methoxy group, or hydroxyl group, with the proviso that a case where both Y and Z are hydrogen atom is excluded, and a compound represented by the following formula (11):

(11)

wherein X and A represents a halogen atom, methoxy group, or hydroxyl group, and Y, Z, B, and C each represents a hydrogen atom, a halogen atom, methoxy group, or hydroxyl group, with the proviso that cases where Y and Z are substituents selected from an atom or groups described above with both B and C being hydrogen atoms and the cases where all of Y, Z, B, and C are hydrogen atoms are excluded.

* * * * *

SEQUENCE LISTING

```
<160> NUMBER OF SEQ ID NOS: 13

<210> SEQ ID NO 1
<211> LENGTH: 501
<212> TYPE: PRT
<213> ORGANISM: Symplectoteuthis oualaniensis

<400> SEQUENCE: 1

Tyr Val Arg Pro Val Ser Ser Trp Lys Val Ala Val Phe Glu His Gln
1               5                   10                  15

Val Ile Pro Pro Lys Thr Asp Met Glu Thr Arg Glu Glu Ala Leu Asp
            20                  25                  30

Ala Leu Lys Leu Asn Ser Asp Val Tyr His Glu Ala Val Leu Glu Ser
        35                  40                  45

Arg Ser Lys Gly Val Lys Met Ile Val Phe Pro Glu Tyr Gly Leu Tyr
    50                  55                  60

Asp Ile Asn Thr Leu Thr Arg Thr Arg Met Asp Leu Met Ala Glu Lys
65                  70                  75                  80

Val Pro His Pro Lys His Gly His Arg Asn Pro Cys Asp Glu Pro Glu
                85                  90                  95

Tyr Gln Thr Gln Ser Ser Glu Met Leu Arg Thr Phe Ser Cys Met Ala
            100                 105                 110

Lys Glu Asn Asp Met Tyr Met Val Val Asn Met Ala Gly Arg Glu Pro
        115                 120                 125
```

```
Cys Arg Arg Ala Thr Glu Pro Glu Cys Pro Gly Asp Lys Gln Leu Leu
130                 135                 140

Tyr Asn Thr Asn Val Ala Phe Asn Asn Glu Gly Asp Val Val Ala Arg
145                 150                 155                 160

Tyr Tyr Lys Thr His Leu Phe Trp Glu Glu Gly Trp Phe Asn Ser Ser
                165                 170                 175

Lys Asn Tyr Glu Met Ala Leu Trp Asp Thr Pro Ile Gly Lys Phe Gly
            180                 185                 190

Thr Phe Met Cys Phe Asp Phe Gln Ala Val Gln Leu Ile Glu Gln Tyr
        195                 200                 205

Asn Val Arg His Ile Ala Tyr Pro Ala Ser Trp Val Asn Leu Pro Pro
210                 215                 220

Ile Tyr Gln Ser Ile Gln Ser His Ser Ala Phe Ala Arg Phe Ala Lys
225                 230                 235                 240

Ile Asn Leu Leu Ala Ala Ser Val His Arg Leu Glu Thr Ser Thr Tyr
                245                 250                 255

Gly Ser Gly Ile Tyr Ser Pro Asn Gly Ala Glu Ile Phe Tyr Phe Arg
            260                 265                 270

Pro Asp Ile Pro Lys Ser Lys Leu Leu Val Ala Glu Ile Leu Pro Ile
        275                 280                 285

His Val Lys Lys Pro Glu Gln Thr Val Val Asn Lys Asp Asn Pro Val
290                 295                 300

Phe Pro Ser Glu Asp Asp Val Gln Asp Leu Phe Asp Arg Gly Asp
305                 310                 315                 320

Phe Ala Phe Leu Lys Tyr Lys Arg Met Thr Thr Arg Ala Gly Thr Val
                325                 330                 335

Glu Val Cys Gln Lys Ser Phe Cys Cys Lys Ala Arg Tyr Ala Val Lys
            340                 345                 350

Asp Arg Phe Lys Glu Val Tyr Ala Val Gly Val Tyr Asp Gly Leu Leu
        355                 360                 365

Ser Ala Gly Ala Asn Asn Leu Tyr Phe Gln Ile Cys Thr Val Ile Gln
370                 375                 380

Cys Pro His Lys Lys Cys Gly Leu Lys Ile Ser Lys Val Arg Thr His
385                 390                 395                 400

Phe Lys Tyr Leu Asn Leu Arg Ala Asp Gly Trp Leu Asp Arg Tyr Val
                405                 410                 415

Phe Pro Ser Tyr Thr Val Met Tyr Asn Asn Tyr Ile Ala Leu Asp Pro
            420                 425                 430

Phe Val Trp Asn Tyr Thr Val Ala Gly Gly Ile Glu Thr Lys Pro Gly
        435                 440                 445

Thr Ser Thr Pro Leu His Ser Ala Asn Leu Val Ala Arg Ile Tyr Ala
450                 455                 460

Lys Asp Ser Ser Lys His Val His Gln Pro His Pro Ile Asp Glu Gly
465                 470                 475                 480

Val Ile Lys Met Ala Val Lys Tyr Met Leu Tyr Val Met Ala Ala Tyr
                485                 490                 495

Val Tyr Ala Ala Ser
            500

<210> SEQ ID NO 2
<211> LENGTH: 370
<212> TYPE: PRT
<213> ORGANISM: Symplectoteuthis oualaniensis
```

-continued

<400> SEQUENCE: 2

```
Ala Thr Glu Pro Glu Cys Pro Gly Asp Lys Gln Leu Leu Tyr Asn Thr
1               5                   10                  15

Asn Val Ala Phe Asn Asn Glu Gly Asp Val Val Ala Arg Tyr Tyr Lys
            20                  25                  30

Thr His Leu Phe Trp Glu Gly Trp Phe Asn Ser Ser Lys Asn Tyr
        35                  40                  45

Glu Met Ala Leu Trp Asp Thr Pro Ile Gly Lys Phe Gly Thr Phe Met
50                  55                  60

Cys Phe Asp Phe Gln Ala Val Gln Leu Ile Glu Gln Tyr Asn Val Arg
65                  70                  75                  80

His Ile Ala Tyr Pro Ala Ser Trp Val Asn Leu Pro Pro Ile Tyr Gln
                85                  90                  95

Ser Ile Gln Ser His Ser Ala Phe Ala Arg Phe Ala Lys Ile Asn Leu
            100                 105                 110

Leu Ala Ala Ser Val His Arg Leu Glu Thr Ser Thr Tyr Gly Ser Gly
        115                 120                 125

Ile Tyr Ser Pro Asn Gly Ala Glu Ile Phe Tyr Phe Arg Pro Asp Ile
130                 135                 140

Pro Lys Ser Lys Leu Leu Val Ala Glu Ile Leu Pro Ile His Val Lys
145                 150                 155                 160

Lys Pro Glu Gln Thr Val Val Asn Phe Asp Asn Pro Val Phe Pro Ser
                165                 170                 175

Glu Asp Asp Val Gln Asp Leu Phe Asp Arg Gly Asp Phe Ala Phe
            180                 185                 190

Leu Lys Tyr Lys Arg Met Thr Thr Arg Ala Gly Thr Val Glu Val Cys
        195                 200                 205

Gln Lys Ser Phe Cys Cys Lys Ala Arg Tyr Ala Val Lys Asp Arg Phe
210                 215                 220

Lys Glu Val Tyr Ala Val Gly Val Tyr Asp Gly Leu Leu Ser Ala Gly
225                 230                 235                 240

Ala Asn Asn Leu Tyr Phe Gln Ile Cys Thr Val Ile Gln Cys Pro His
                245                 250                 255

Lys Lys Cys Gly Leu Lys Ile Ser Lys Val Arg Thr His Phe Lys Tyr
            260                 265                 270

Leu Asn Leu Arg Ala Asp Gly Trp Leu Asp Arg Tyr Val Phe Pro Ser
        275                 280                 285

Tyr Thr Val Met Tyr Asn Asn Tyr Ile Ala Leu Asp Pro Phe Val Trp
290                 295                 300

Asn Tyr Thr Val Ala Gly Gly Ile Glu Thr Lys Pro Gly Thr Ser Thr
305                 310                 315                 320

Pro Leu His Ser Ala Asn Leu Val Ala Arg Ile Tyr Ala Lys Asp Ser
                325                 330                 335

Ser Lys His Val His Gln Pro His Pro Ile Asp Glu Gly Val Ile Lys
            340                 345                 350

Met Ala Val Lys Tyr Met Leu Tyr Val Met Ala Tyr Val Tyr Ala
        355                 360                 365

Ala Ser
370
```

<210> SEQ ID NO 3
<211> LENGTH: 1646
<212> TYPE: DNA
<213> ORGANISM: Symplectoteuthis oualaniensis

```
<400> SEQUENCE: 3
ttcgagcatc aggtcattcc tccaaaaaca gatatggaga ctcgagagga ggccctggac    60
gcactcaaat tgaatagcga tgtctatcat gaagcagtgc ttgaatcaag atcaaaagga   120
gtcaaaatga ttgtcttccc cgaatatggt ctttatgata tcaacacatt gacaagaacg   180
aggatggacc tgatggcaga gaaagttcca caccctaaac acggccaccg aaacccatgc   240
gatgagccag agtatcaaac tcaaagttca gagatgttga aactttcag ttgtatggcg    300 aaagaaaatg atatgtatat ggtggtcaac atggccggtc gtgagccatg taggcgtgcc   360
actgaacctg agtgcccagg agacaagcaa ttgctataca acactaatgt tgcttttaac   420
aatgaaggtg acgttgttgc aaggtattac aaaacccatc tattttggga agaaggttgg   480
ttcaactcgt ccaagaatta cgaaatggca ctttgggaca ccccgattgg caaatttggt   540
acttttatgt gttttgactt ccaggctgtt caactaatcg aacaatataa cgtacgacat   600
attgcttacc cagcttcctg ggttaatctg cccccaatct atcaatcaat ccaatcccat   660
tcagcttttg ctcgttttgc aaagattaat ctattggcag caagtgtcca caggctagag   720
accagtacct atggtagcgg catatattca cctaatggag ctgaaatctt ttatttccgt   780
ccagacattc aaaaagtaa actgttagtg gccgagattt taccaatcca tgttaaaaaa    840
ccagagcaga cggtagtcaa ttttgataat cccgtattcc cgtctgaaga tgatgacgtg   900
caagatcttt tgatcgggg cgactttgct ttcttaaaat ataaacgtat gacaaccagg    960
gctggtacag tggaagtttg ccaaaagtcc ttctgttgca aagctcgcta tgcagtcaaa  1020
gatcgattca agaagttta cgctgtgggt gtctatgacg gtttattatc tgccggtgcc   1080
aacaatctct acttccagat ttgtacggtg attcaatgtc ctcataagaa gtgcggactg  1140
aaaatatcaa agtaaggac tcatttcaag taccttaatt tgcgagcaga tggatggtta   1200
gatagatacg tgtttccttc atatacggta atgtacaaca attacattgc gcttgatcca  1260
tttgtatgga attatacagt ggccggagga atcgaaacta accaggcac aagcactcct   1320 ctacattcag ccaatctggt cgcaaggatt tatgcaaaag acagttcaaa gcacgtccat  1380
cagccacatc ctattgacga aggcgtaatt aaaatggccg ttaaatatat gttatatgta  1440
atggcagctt atgtttacgc cgcctcctaa atatcgaaaa taaacattgg accactcgaa  1500
aacctcatcg aatgatgatg ctgaaagatt agggatttat gaataatgct ttttcaattc  1560
ttggtggtgg tgctgcttaa aaaattatgc gaatactttg cacgaacttt aaaagtttag  1620
atcaagatga tttccatgaa aaaatc                                        1646

<210> SEQ ID NO 4
<211> LENGTH: 28
<212> TYPE: DNA
<213> ORGANISM: Artificial Sequence
<220> FEATURE:
<223> OTHER INFORMATION: Primer for PCR cloning
<220> FEATURE:
<221> NAME/KEY: misc_feature
<222> LOCATION: (23)..(23)
<223> OTHER INFORMATION: Nucleotide 23 is "n" wherein "n" = any
      nucleotide.

<400> SEQUENCE: 4
cgggatcctt ygarcaycar gtnathcc                                        28
```

```
<210> SEQ ID NO 5
<211> LENGTH: 28
<212> TYPE: DNA
<213> ORGANISM: Artificial Sequence
<220> FEATURE:
<223> OTHER INFORMATION: Primer for PCR cloning
<220> FEATURE:
<221> NAME/KEY: misc_feature
<222> LOCATION: (20)..(23)
<223> OTHER INFORMATION: Nucleotides 20 and 23 are "n" wherein "n" = any
      nucleotide.

<400> SEQUENCE: 5
gcctcgagtc rtrrttraan gcnacrtt                                              28

<210> SEQ ID NO 6
<211> LENGTH: 20
<212> TYPE: DNA
<213> ORGANISM: Artificial Sequence
<220> FEATURE:
<223> OTHER INFORMATION: Primer for PCR cloning

<400> SEQUENCE: 6
atggacctga tggcagagaa                                                       20

<210> SEQ ID NO 7
<211> LENGTH: 26
<212> TYPE: DNA
<213> ORGANISM: Artificial Sequence
<220> FEATURE:
<223> OTHER INFORMATION: Primer for PCR cloning
<220> FEATURE:
<221> NAME/KEY: misc_feature
<222> LOCATION: (9)..(21)
<223> OTHER INFORMATION: Nucleotides 9, 12, 15 & 21 are "n" wherein
      "n" = any nucleotide.

<400> SEQUENCE: 7
tgrtadatng gnggnargtt naccca                                                26

<210> SEQ ID NO 8
<211> LENGTH: 20
<212> TYPE: DNA
<213> ORGANISM: Artificial Sequence
<220> FEATURE:
<223> OTHER INFORMATION: Primer for PCR cloning
<220> FEATURE:
<221> NAME/KEY: misc_feature
<222> LOCATION: (6)..(6)
<223> OTHER INFORMATION: Nucleotide 6 is "n" wherein "n" = any
      nucleotide.

<400> SEQUENCE: 8
gtytgnacrt crtcrtcytc                                                       20

<210> SEQ ID NO 9
<211> LENGTH: 23
<212> TYPE: DNA
<213> ORGANISM: Artificial Sequence
<220> FEATURE:
<223> OTHER INFORMATION: Primer for PCR cloning

<400> SEQUENCE: 9
gagaccagta cctatggtag cgg                                                   23

<210> SEQ ID NO 10
<211> LENGTH: 28
<212> TYPE: DNA
<213> ORGANISM: Artificial Sequence
```

```
<220> FEATURE:
<223> OTHER INFORMATION: Primer for PCR cloning

<400> SEQUENCE: 10
ttgaattccc aaaaacagat atggagac                                28

<210> SEQ ID NO 11
<211> LENGTH: 28
<212> TYPE: DNA
<213> ORGANISM: Artificial Sequence
<220> FEATURE:
<223> OTHER INFORMATION: Primer for PCR cloning

<400> SEQUENCE: 11
ttgaattcct attttgggaa gaaggttg                                28

<210> SEQ ID NO 12
<211> LENGTH: 31
<212> TYPE: DNA
<213> ORGANISM: Artificial Sequence
<220> FEATURE:
<223> OTHER INFORMATION: Primer for PCR cloning

<400> SEQUENCE: 12
aagtcgactt aggaggcggc gtaaacataa g                            31

<210> SEQ ID NO 13
<211> LENGTH: 9
<212> TYPE: PRT
<213> ORGANISM: Artificial Sequence
<220> FEATURE:
<223> OTHER INFORMATION: N-terminal amino acid sequence

<400> SEQUENCE: 13

Tyr Val Arg Pro Val Ser Ser Trp Lys
  1               5
```